United States Patent [19]

Porter

[11] Patent Number: 4,742,708

[45] Date of Patent: May 10, 1988

[54] APPARATUS FOR ELECTROCHEMICAL SENSOR CALIBRATION

[75] Inventor: Ronald G. Porter, Anaheim Hills, Calif.

[73] Assignee: Beckman Industrial Corporation, Santa Ana, Calif.

[21] Appl. No.: 51,475

[22] Filed: May 18, 1987

Related U.S. Application Data

[63] Continuation of Ser. No. 896,082, Aug. 13, 1986, abandoned.

[51] Int. Cl.$^4$ .............................................. G01N 37/00
[52] U.S. Cl. ...................................................... 73/1 G
[58] Field of Search .............. 73/1 G; 220/230, 203, 220/204, 209, 202, 253, 315, 360, 366

[56] References Cited

U.S. PATENT DOCUMENTS

| | | | |
|---|---|---|---|
| 4,110,552 | 8/1978 | Lombardi | 220/230 |
| 4,151,739 | 5/1979 | Breuer et al. | 73/1 G |
| 4,209,300 | 6/1980 | Thibault | 73/1 G |
| 4,254,797 | 3/1981 | Mayeaux | 73/1 G |
| 4,322,964 | 5/1972 | Melgaard et al. | 73/1 G |
| 4,351,802 | 9/1982 | Baylis et al. | 73/864.83 |
| 4,411,151 | 10/1983 | Kessler et al. | 73/1 G |
| 4,462,244 | 7/1984 | Lee | 73/1 G |
| 4,489,590 | 12/1984 | Hadden | 73/1 G |
| 4,577,788 | 3/1986 | Richardson | 224/273 |
| 4,590,789 | 5/1986 | Kunze | 73/1 G |
| 4,689,135 | 8/1987 | Lungu et al. | 73/1 G |

*Primary Examiner*—Stewart J. Levy
*Assistant Examiner*—Robert R. Raevig
*Attorney, Agent, or Firm*—John E. Vanderburgh

[57] ABSTRACT

Apparatus for removably connecting a calibrating gas chamber to the body of an electrochemical sensor consisting of corresponding members carried by the sensor and the gas chamber, each member defining a contact surface that cooperates with the contact surface of the corresponding member to removably secure the surface together so that connection of the chamber is accomplished by contacting the surfaces of the corresponding members and the chamber can be removed when calibration of the sensor is finished for connection to another sensor or reconnection to the same sensor at a later time. In a preferred embodiment the corresponding members are composed of Velcro fabric.

1 Claim, 1 Drawing Sheet

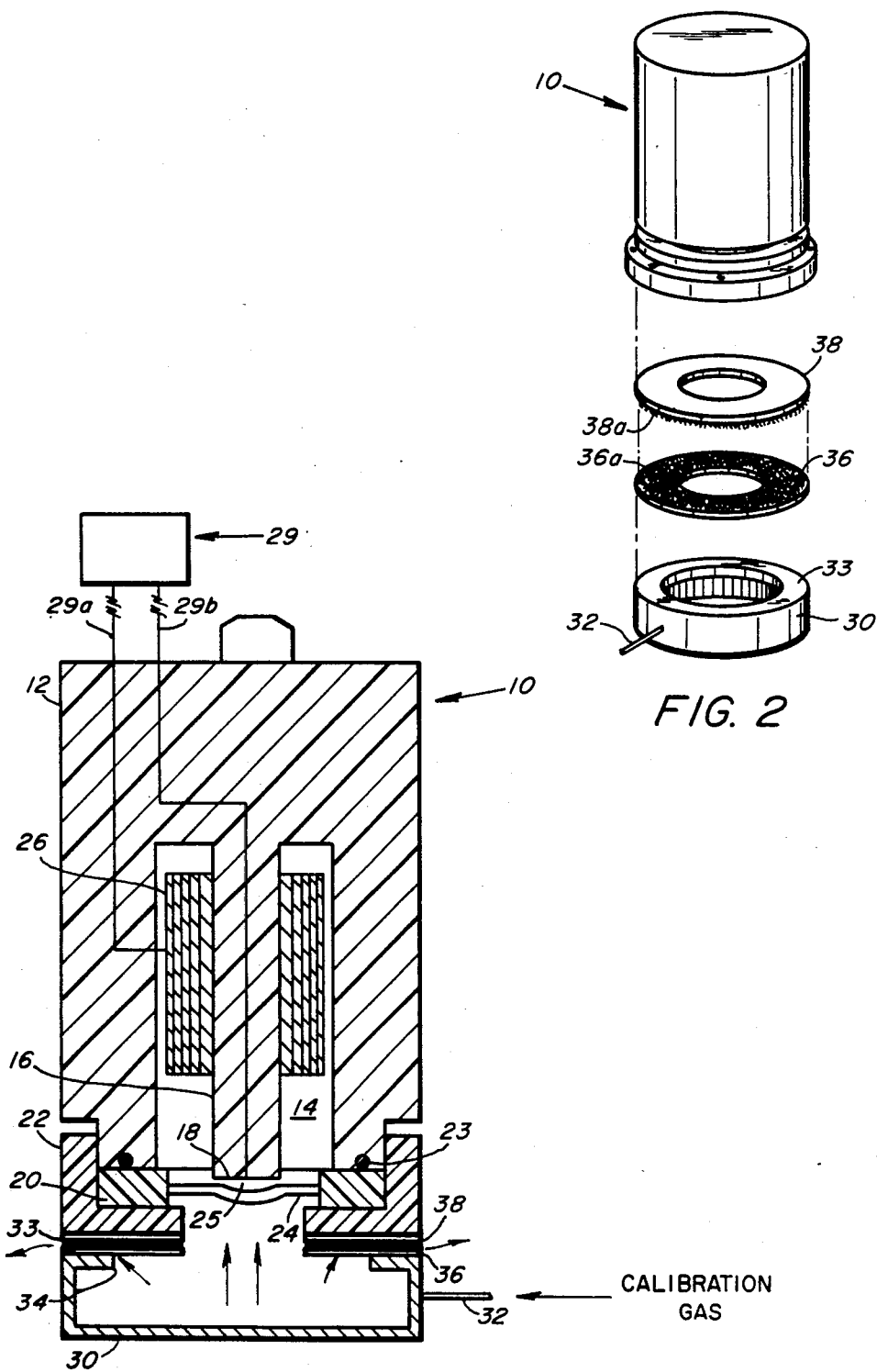

APPARATUS FOR ELECTROCHEMICAL SENSOR CALIBRATION

This application is a continuation of application Ser. No. 896,082, filed Aug. 13, 1986, now abandoned.

FIELD OF THE INVENTION

The invention relates to electrochemical gas detection systems and more particularly to means for connecting a source of gas into such systems.

BACKGROUND OF THE INVENTION

Electrochemical devices for the detection of gases in fluid medium are important tools for the monitoring and control of various processes. For example, electrochemical sensors are utilized for air quality monitoring as well as for monitoring automobile exhaust and for controlling various industrial processes. The sensors generally operate to produce a signal, such as a current flow between electrodes, which is directly proportional to the concentration or the partial pressure of the gas being tested in the sample.

In the operation of electrochemical sensors, it is customary to periodically calibrate the zero and span performance of the sensor in order to re-confirm or re-establish the measurement accuracy. Calibration of the sensor elements is important in achieving accurate measurement with the sensor because sensors tend to have some zero drift over time in either a positive or negative direction. In accordance with conventional practice, the zero drift of the sensor element over time is compensated for or adjusted by periodic zero calibrations utilizing a known zero calibration gas composition which contains none of the gas being tested for. A similar problem exists with respect to the sensor span signal which gradually will change over a peiod of time due to aging of the sensor elements. This may similarly be corrected for or adjusted by periodic span calibrations of the sensor circuitry utilizing a calibration gas which contains a known quantity of test gas.

Calibration of the instrument can be a substantial operational problem since the instrument is normally taken off line and often removed to a suitable facility, such as a laboratory, for calibration where the calibration gas is introduced to the sensor elements. In many situations, such as in the case of industrial controls, the removal of the sensor from the control process may result in the loss of production time and considerable expense due to the process being normally shut down in the absence of control instrumentation. In the alternative, to avoid shut down of the process being monitored substitute instruments are used to replace the instruments being calibrated thus requiring a larger inventory of replacement instruments than required if the need to substitute instruments during the calibration process can be eliminated.

Methods and apparatus to automate the calibration process on line thereby eliminating the need for any substantial process shut down or equipment substitutions have been utilized, such as for example in U.S. Pat. No. 4,322,964 which provides a fluidic gate for the introduction of the calibration gas to an analyzer, or U.S. Pat. No. 4,489,590 which provides a method for automatically calibrating gas detectors which are monitoring combustible gases. However, such devices substantially add to the cost of the instrument and may not be suitable for many applications, such as for example, the monitoring of industrial atmospheres for toxic gases and the like.

Accordingly it would be desirable to provide low cost apparatus for easily and conveniently introducing calibration gases to sensors at their location without the necessity of moving the sensor or taking it out of service for any substantial period of time.

SUMMARY OF THE INVENTION

The invention is directed to apparatus for removably connecting an electrochemical sensor to a source of gas. Although the particular gas source is not critical, the invention will be described hereinafter in connection with the calibration of electrochemical sensors. Thus the sensor may be connected to a source of gas, i.e., a carrier gas which contains none of the tested-for gas sample or to a span gas, i.e., a carrier gas which contains a known quanitity of the tested-for gas sample.

In accordance with the present invention, an electrochemical detection system includes a detector comprising an electrochemical sensor and circuit means connecting the sensor to a source of power and to amplification and display means for amplifying and displaying the sensor signal. The detector housing is adapted by quick disconnect means for removably connecting a second body defining a calibration chamber to the detector housing for communication between the housing and the sensor. The chamber is connected to a source of gas, which is introduced into the chamber for contact with the sensor.

The electrochemical sensor may be of any design but generally will include a body which defines a reservoir for electrolyte and in which is disposed an anode and a cathode which are electrically connected by the electrolyte. Leads run from the electrodes to a source of power and suitable amplification and measurement instrumentation to complete the circuitry. The sensor body is open at one end and one of the electrodes, normally the cathode, is disposed adjacent this opening. A gas permeable membrane is disposed over the opening to retain the electrolyte within the reservoir and to permit the diffusion of the tested-for gas for contact with the cathode of the sensor.

In accordance with the invention the body defining a calibration chamber is connected to a source of calibrating gas, either span gas or zero gas or both, and is removably attached to the sensor for communication between the chamber and the gas permeable membrane of the sensor by attachment means comprising locking members provided on the chamber and on the sensor which upon contact with each other cooperate to attach the chamber to the sensor and which can be nondestructively parted to permit removal of the chamber upon completion of the calibration operation.

The calibration chamber body attachment means is nonmechanical and comprises corresponding members carried by the detector or sensor body and by the chamber. The members are provided with surfaces which upon contact grip one another so that the chamber and sensor can be connected and which surfaces can be parted without destruction by simply pulling the chamber body away from the sensor. For example the connecting members may comprise magnetic components of sufficient strength to hold the chamber body in position while calibrating the instrument yet which permit ready removal of the chamber body when calibration is finished. In another embodiment of the invention the connecting members may comprise interlocking fabric components, such as VELCRO fabric (VELCRO is a trademark of the Dow Chemical Company).

In a preferred embodiment of the invention, the chamber body is adapted to permit the leakage of gas contained therein should the pressure within the chamber exceed atmospheric pressure. In this fashion damage to the gas permeable membrane of the sensor is avoided.

In a more preferred embodiment of the invention the locking members are themselves gas permeable such as by the provision of pores or passages through the members so that should pressure within the chamber exceed atmospheric pressure the gas contained therein will pass through the pores or passages of the locking members to the atmosphere.

In accordance with a preferred form of the invention, the source of calibration gas to which the calibration gas chamber is connected is portable and may include one or more tanks containing the span gas and the zero gas carried on a dolly, or other suitable conveyance, for movement of the calibration gases from place to place as required.

Other aspects and advantages of the present invention will become apparent from the following detailed description taken in conjunction with the drawings.

BRIEF DESCRIPTION OF THE DRAWINGS

FIG. 1 is an exploded perspective view of an electrochemical sensor including connecting members and a body defining a calibration chamber for source gas, and FIG. 2 is a sectional elevation of an electrochemical sensor to which is connected a body defining a calibration chamber for source gas in accordance with the invention.

DETAILED DESCRIPTION OF THE INVENTION

For purposes of illustration the invention will be described herein in conjunction with the calibration of an electrochemical sensor utilized for the detection of carbon monoxide in the atmosphere. The zero gas utilized to calibrate the instrument zero is air free of carbon monoxide and the span gas is air which contains 80 ppm carbon monoxide. Although the calibration period is not critical to the invention, electrochemical sensors of this type are normally calibrated at least once a month and preferably once a week.

Referring to the figures, a typical electrochemical sensor for the detection of carbon monoxide is indicated generally as 10. The sensor 10 comprises a body 12 having a reservoir 14 therein which contains a center post 16 for supporting a cathode 18 at its lower end. A membrane holder 20, cap 22 and O-ring 23 are provided to clamp a polymeric membrane material 24 over the cathode 18 thereby closing the reservoir 14. The polymeric material is selected from any of the gas permeable compositions known in the art, such as for example polytetrafluoroethylene. The membrane 24 may have a thickness of from about 0.00025 inches to about 0.002 inches. The membrane holder 20 may be of any suitable and commonly known design and serves to maintain the membrane 24 in a stretched position over the cathode 18. The reservoir 14 is filled with a suitable electrolyte, typically a five percent KC1 solution, either buffered or unbuffered. Although exaggerated in the FIG. 2, a space 25 is provided between the cathode 18 and the membrane 24 which is occupied by a thin film of electrolyte. An anode 26, generally a noble metal such as platinum or silver, is disposed within the reservoir 14 in contact with the electrolyte. A potential is applied between the anode 26 and the cathode 18 by circuit means, shown generally as 29 and leads 29a and 29b extend between the circuit means 29 and the cathode 18 and the anode 26 respectively. Electrical connection between the anode 26 and the cathode 18 is completed by the electrolyte.

As indicated, the outer surface of the membrane 24 is exposed to the atmosphere being tested and the test gas, in this case carbon monoxide, permeates through the membrane 24 to contact the cathode 18 in the presence of the electrolyte 26. The contact between the cathode 18 and the carbon monoxide produces a current flow between the cathode 18 and anode 26 which is amplified by the circuit means to a recordable signal. The amount of current flow is directly proportional to the partial pressure of carbon monoxide contacting the cathode 18.

It will be apparent that in its normal sensing mode, the membrane 24 is exposed to the atmosphere for sensing the presence of carbon monoxide. However, to effect calibration of the instrument it is necessary to contact the membrane with a known calibration under conditions sufficiently controlled to accurately calibrate the instrument and in a manner which does not result in undue pressure on the membrane which would damage it. As illustrated in FIGS. 1 and 2, this is accomplished in accordance with the present invention by a removable chamber body 30 which is provided with inlet line 32 connected to a source of calibration gas, not shown. The upper edge of the side wall of the chamber body 30 extends radially inwardly to define an annular upper surface 33 and an opening 34 which provides communication between the interior of the chamber body and the membrane 24 of the sensor 10. A locking member 36 is disposed around the upper surface of the chamber body 30 and is securely fixed thereto, such as by adhesive bonding. A corresponding locking member 38 is disposed on the bottom surface of the body 12 of the sensor 10 for contact with the locking element 36 of the chamber body 30 to effect connection of the chamber body to the sensor. As illustrated in FIG. 2, the locking members 36 and 38 are annular shaped fabric members which are glued to the chamber body 30 and the lower surface of the sensor body 12 and which have opposing contact surfaces 36a and 38a. The contact surface 36a of the member 36 has a plurality of small fiber loops while the cooperating contact surface 38a of the member 38 is provided with a plurality of small fiber hooks which engage the loops of the contact surface 36a to secure the respective contact surfaces together. Fabric of this construction is available under the trademark VELCRO. Fabrics of the type are preferred because of the cooperating surfaces which secure the two members upon contact. The surfaces can be nondestructively disengaged and refastened. The gripping strength between locking member 36 and 38 when formed of such fabric is sufficient to retain the chamber body 30 in position on the sensor 10 during the period in which the calibration gas is introduced into the chamber body for calibration of the sensor. In addition, however, materials such as VELCRO have a porous structure which permits the flow of calibration gas from the chamber body 30 through the members 36 and 38 into the atmosphere in the event that pressure within the chamber body exceeds atmospheric pressure. This feature prevents damage to the sensor membrane 24 should pressure within the chamber body 30 exceed atmospheric pressure for any reason.

It will be clear, however, that other types of contact materials may serve as the locking members 36 and 38 of the present invention. For example, resilient magnetic materials, such as silicone rubber filled with magnetic particles, are highly suitable and they are readily formed to the configuration of the chamber body 30 and the sensor 10. The magntic properties of such materials provide the desired removable contact action to permit ready attachment of the chamber body 30 to the sensor 10 without manipulation and undue loss of time. With such materials, however, it is highly preferred that grooves or passages be provided to permit the outflow of calibration gas in the event of excessive back pressure within the chamber body 30.

As illustrated in the drawings, the locking members 38 and 36 are generally annularly shaped members to conform with the configuration of the mating surfaces of the chamber body 30 and the sensor 10. However, the configuration of the locking members 36 and 38 is not critical so long as there is sufficient contact surface to provide the gripping or attachment strength necessary to maintain the chamber body 30 in position on the sensor 10 during the calibration operation yet permit ready separation of the gripping surfaces for easy removal of the chamber body from the sensor. It will also be clear that under proper circumstances only a single locking member may be required to effect the removable connection of the chamber body 30 to the sensor 10. For example, should the cap 22 of the sensor 10 or the chamber body 30 itself be constructed of steel or other material capable of being attracted by magnetic force, only a single magnetic locking member is required to retain the chamber body 30 in its position on the sensor.

While the invention has been specifically described with respect to specific embodiments thereof, it will be appreciated that various modifications, variations and adaptations may be made within the spirit and scope of the present disclosure, which are intended to be within the scope of the following claims.

What is claimed is:

1. An electrochemical gas detection system comprising an electrochemical sensor having a housing defining a reservoir for electrolyte, an anode and a cathode disposed in said reservoir for contact with electrolyte contained therein, said housing having an opening in one surface thereof for communication between the reservoir and the exterior of said housing, a gas permeable, electrolyte impermeable membrane sealing said opening, means connecting said anode and cathode to a source of power and amplification and measurement instrumentation, a calibration system including a body having an interior chamber and open at one end, said body being removably attached to said housing with its open end in alignment with the opening in said housing for communication between the gas permeable, electrolyte impermeable membrane and the body interior to define a calibration chamber for said electrochemical sensor and means including a source of calibration gas for leading said calibration gas into said calibration chamber, the improvement comprising a fabric attachment member carried on said housing surface adjacent the opening therein and a corresponding fabric attachment member disposed on an opposing surface of said body adjacent the opening to the interior thereof, each said fabric attachment member having a surface for cooperation with the surface of the corresponding member to removably secure said housing and said body for calibration of said electrochemical sensor, said attachment members permitting the diffusion of calibration gas from the calibration chamber in the event calibration gas pressure exceeds atmospheric pressure thereby to maintain essentially atmospheric pressure on said gas permeable, electrolyte impermeable membrane during calibration of said electrochemical sensor.

* * * * *